United States Patent [19]
Vandenberg

[11] Patent Number: 5,665,080
[45] Date of Patent: Sep. 9, 1997

[54] OROPHARYNEAL SUCTIONING DEVICE

[76] Inventor: James T. Vandenberg, 3405 Beth Ct. NE., Lacey, Wash. 98516

[21] Appl. No.: 613,251

[22] Filed: Mar. 8, 1996

[51] Int. Cl.$^6$ .............................. A61M 1/00; A61M 16/00
[52] U.S. Cl. ........................ 604/319; 64/317; 128/207.14
[58] Field of Search ........................ 128/202.28, 202.27, 128/207.14, 207.15; 604/317–319, 119, 163

[56] References Cited

U.S. PATENT DOCUMENTS

| | | | |
|---|---|---|---|
| 4,273,126 | 6/1981 | Grane et al. | |
| 4,319,570 | 3/1982 | Grane | |
| 4,455,140 | 6/1984 | Joslin | |
| 4,662,367 | 5/1987 | Gore, Jr. | |
| 4,747,843 | 5/1988 | Felix et al. | 604/319 |
| 4,925,447 | 5/1990 | Rosenblatt | |
| 5,002,534 | 3/1991 | Rosenblatt | 604/319 |
| 5,114,415 | 5/1992 | Shedlock | |
| 5,141,503 | 8/1992 | Sewell, Jr. | 604/317 |
| 5,167,621 | 12/1992 | Band et al. | 604/319 |
| 5,251,619 | 10/1993 | Lee | 128/207.15 |
| 5,261,897 | 11/1993 | Kurtz et al. | 604/317 |
| 5,419,769 | 5/1995 | Devlin et al. | |
| 5,509,408 | 4/1996 | Kurtis | 128/207.14 |

*Primary Examiner*—John G. Weiss
*Assistant Examiner*—David J. Cho
*Attorney, Agent, or Firm*—Richard C. Litman

[57] ABSTRACT

An oropharyngeal suctioning device for evacuation of vomitus from patients having an altered gag reflex using an increased diameter tubing and similarly increased diameter suction tip having an inside diameter of ½ inch to 1 inch, which combination provides an evacuation rate of at least 10 times faster than the rate of evacuation using the prior art. The oropharyngeal suctioning device includes a suction tip having an increased diameter ranging between ½ inch and one inch, a patient vacuum tubing of an inside diameter between ½ inch to one inch and 4 to 10 feet in length, a first adapter for attaching the tubing to the 1 inch inside diameter pour spout of a suction canister and a second adapter for connecting the suction tip and the patient vacuum tubing. A central vacuum line inlet is provided to apply negative pressure to the canister.

2 Claims, 2 Drawing Sheets

OROPHARYNEAL SUCTIONING DEVICE

BACKGROUND OF THE INVENTION

1. FIELD OF THE INVENTION

The present invention relates to an improved oropharyngeal suctioning device for rapid evacuation of fluid foreign material including chunky vomitus and bodily secretions.

2. DESCRIPTION OF THE PRIOR ART

In emergency and surgical care hospital and medical provider settings, aspiration of regurgitated gastric contents in patients with an altered gag reflex (e.g., unconscious or anesthetized) is a life-threatening event. Mortality rates as high as seventy percent have been associated with massive aspiration of gastric contents. It is known that as little as twenty milliliters of gastric contents (approximately ⅕ mouthful) can cause significant lung damage when aspirated.

Treatment is simple: evacuation of the airway of the patient prevents the foreign matter from passing from the oropharyngeal cavity into upper airway passages and beyond. However, two factors affect the success of treatment. First, the time needed to evacuate the oropharyngeal cavity and airway of a patient is obviously of the essence; if vomitus can be expeditiously removed, patient morbidity and mortality should be positively influenced. Second, complete removal of vomitus and secretions is also important to prevent aspiration of secretions and minute particles after the bulk of the vomitus has been removed. Moreover, the medical care provider must maintain a sensitivity to possible soft-tissue damage within the oropharyngeal cavity caused by the suction tip during overzealous suctioning. Thus, a balance must be maintained between the need for speedily clearing a large volume of variably sized vomitus and the need for precise removal of residual secretions. Under ideal medical care provider circumstances, removal of the regurgitated materials begins immediately after emesis. A commonly employed suction system comprises a thick-walled vacuum tubing (usually ¼ inch inside diameter, 8 to 10 feet in length,) with a suction tip for collection of vomitus from the oropharynx of a patient. The tubing is connected to a collection canister attached to a wall-mounted vacuum inlet or regulator, in turn connected to a central vacuum line. Standard hospital regulations require that central vacuum line systems must be capable of generating at least 304 mm Hg at any inlet, the norm ranging between 381 mm Hg and 482 mm Hg.

However, surprisingly, such standard and commonly used hospital suction equipment is inadequate for removing both chunky vomitus and the remaining secretions. Medical literature reveals that a standard hospital setup having a vacuum pressure of 550 mm Hg required 7.5 seconds to evacuate 140 milliliters of simulated vomitus, a period of time concluded to be too long to prevent clinically significant aspiration.

Moreover, commonly used suctioning tips, such as Yankauer tips also having a ¼ inch inside diameter or less, are designed primarily for applications wherein a capability to evacuate every drop of essentially solid-free liquids or secretions (at most contaminated by small solid chips such as might be encountered during surgery) from a surface is desired. However, such tips become easily and entirely blocked by chunky vomitus. Clearing the blockage in an emergency situation requires additional precious time. Thus, reliable and effective suction equipment capable of clearing the oropharynx of secretions and chunky vomitus in a timely manner is a critical component of an emergency resuscitation procedure.

The present invention reduces the evacuation time by improving suction efficiency of such hospital suction setups. Increasing the diameter of suction tips, tubing, and connectors leading to the suction port of a suction canister increases the rate of flow through the suction device. No studies of the medical literature were found addressing suction device internal diameters to improve suction efficiency.

The prior art likewise discloses no suction apparatus or combination of components thereof having the critical range of diameter for applications suitable to the rapid evacuation of fluid foreign material including chunky vomitus and bodily secretions, nor any combination of structural components directed at improving the rate of fluid flow of secretions containing solid particles to a remote collection container. U.S. Pat. No. 4,273,126 issued Jun. 16, 1981 to Grane et al. describes a hand-held attachment device for use with a tracheal aspirator directed at collection of large, solid particles from the trachea and mouth of a patient. The device provides a stiff suction inlet tube of 200–300 millimeters in length and having an inside diameter of a suggested range of 6 to 12 millimeters (less than ½ inch) to permit secretions including large solid particles to pass therethrough; however, nowhere is the range disclosed to be associated with an evacuation rate dependent upon the tube diameter. The '126 invention links the size of the tubing only to the size of the particles intended to be evacuated; therefore, tubing size may be arbitrarily altered to accommodate the '126 invention.

Other patents reveal a wide range of applications for suction collection devices, none of which describe a combination of similar structural components directed at improving the rate of fluid flow of secretions containing solid particles to a collection container. For example, U.S. Pat. No. 4,455,140 issued Jun. 19, 1984 to Joslin describes a collapsible fluid collection device having telescopically disposed members directed at reducing its storage space. U.S. Pat. No. 4,319,570 issued Mar. 16, 1982 to Grane describes a tracheal suction pump driven by compressed gas and designed primarily for aspiration of vomitus and secretions. U.S. Pat. No. 4,925,447 issued May 15, 1990 to Rosenblatt describes an aspirator containing a bellows to isolate gases and liquids collected from the patient from the source of the suction. U.S. Pat. No. 5,419,769 issued May 30, 1995 to Devlin et al. describes a suction system employing a suction control device which allows manual control of application of reduced pressure in the system. U.S. Pat. No. 4,662,367 issued May 5, 1987 to Gore, Jr. describes a trachea suction tube for removing an obstruction by placing one end over laryngeal surfaces of a patient and by orally drawing air through the tube from the other end. U.S. Pat. No. 5,114,415 issued May 19, 1992 to Shedlock describes a soft, flexible adapter shallowly inserted into the nostril for suctioning secretions from upper airways.

None of the above inventions and patents, taken either singly or in combination, is seen to describe the instant invention as claimed.

SUMMARY OF THE INVENTION

The present invention relates to an improved oropharyngeal suctioning device for rapid evacuation of fluid foreign matter, defined herein as including vomitus and bodily secretions. The oropharyngeal suctioning device for evacuation of vomitus removed from patients having an altered gag reflex using a ¾ inch inside diameter tubing and similarly increased diameter suction tip provides an evacuation rate of at least 10 times faster than the rate of evacuation using the prior art. The oropharyngeal suctioning device includes a suction tip having an increased diameter ranging between ½ inch and 1 inch, a patient vacuum tubing of an inside diameter between ½ inch and 1 inch and 4 to 10 feet in length, a first adapter for attaching the tubing to a pour spout measuring 1 inch inside diameter of a suction canister and a second adapter for connecting the suction tip and the tubing. A central vacuum line inlet is provided to apply negative pressure to the canister.

Accordingly, it is a principal object of the invention to provide an oropharyngeal suctioning device for the rapid evacuation of fluid foreign matter including vomitus and bodily secretions from the oropharyngeal cavity to positively affect the morbidity and mortality of patients subject to a risk of aspiration of fluid foreign matter.

It is another object of the invention to provide an oropharyngeal suctioning device having an increased internal diameter permitting the rapid evacuation of fluid foreign matter.

It is a further object of the invention to provide an oropharyngeal suctioning device having components adapted for use with components of suctioning devices found in the prior art.

Still another object of the invention is to provide an oropharyngeal suctioning device having components which permit an evacuation procedure to be conducted in a standard medical care facility setting.

It is an object of the invention to provide improved elements and arrangements thereof in an apparatus for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

The present invention relates to an improved oropharyngeal suctioning device for rapid evacuation of fluid foreign material including chunky vomitus and bodily secretions wherein a range of internal diameters of the components of a suction system connected to a central vacuum line improves suction efficiency for the intended purpose.

As matter of background, the rate of flow through a uniform tube as defined by Poiseuille's Law is controlled by the following variables: the pressure difference applied, the length of the tube, the viscosity coefficient of the fluid, and the radius of the tube. Poiseuille's Law is stated as follows:

$$R = (p_1 - p_2)(\pi r^4)/8\eta L$$

where R is rate of flow; $p_1 - p_2$ is the pressure difference applied; r is the radius of the tube; $\eta$ is the viscosity coefficient; and, L is the length of the tube.

Figure 2:
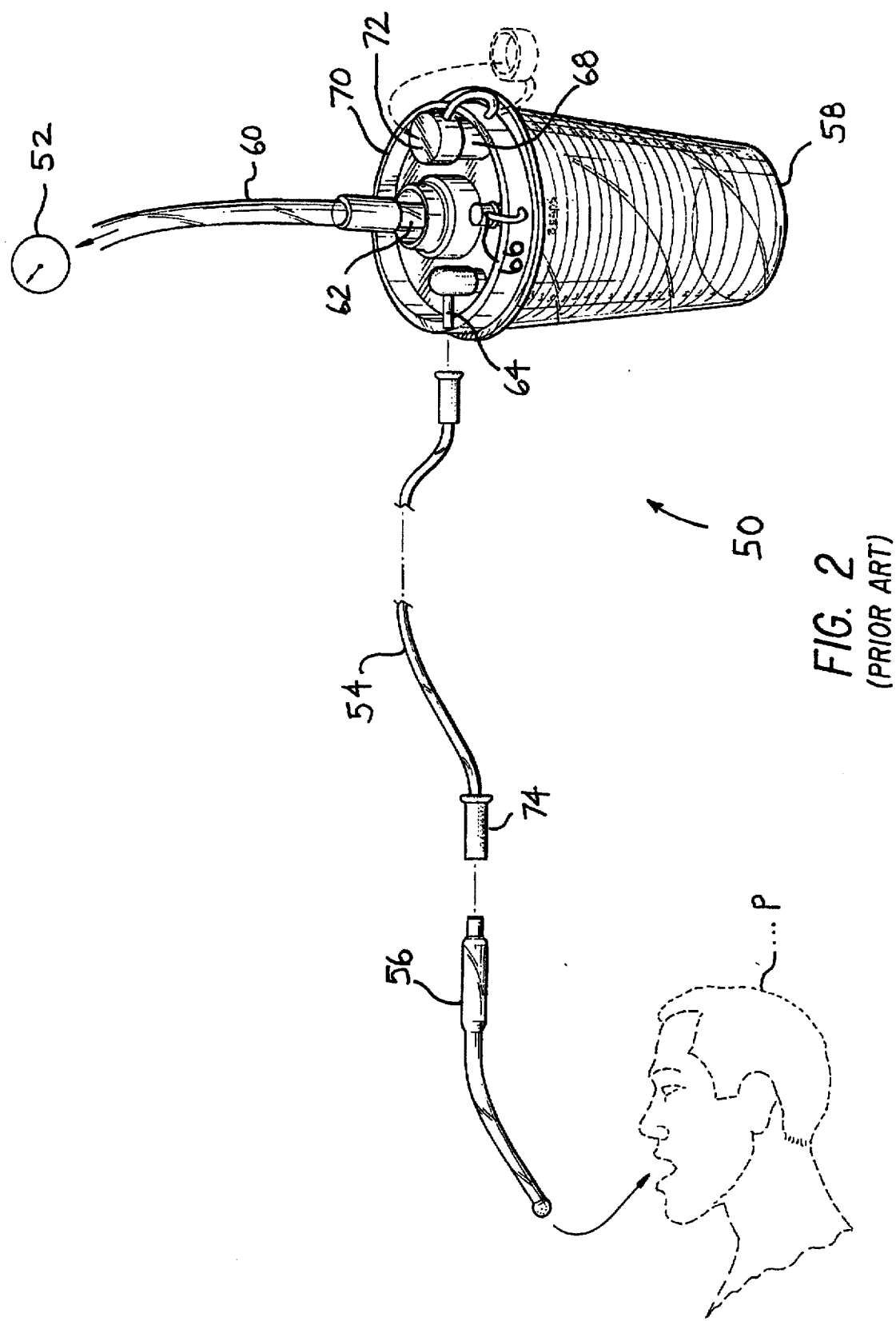
FIG. 2 is an environmental, perspective, exploded view of an oropharyngeal suction device as known in the prior art showing its components and connections.

In the present application of Poiseuille's Law, all variables but the radius of the tube are limited by external factors. Referring first to FIG. 2, the limiting factors can be explained relative to a commonly used suctioning system 50 as found in the prior art.

First, the pressure difference variable is dependent upon the negative pressure source normally supplied at the wall inlet of a central vacuum line of a hospital or medical care provider facility (as represented by the regulator dial 52), which negative pressure as previously noted ranges between 381 mm Hg and 482 mm Hg. Moreover, an optimal suction pressure has been described in medical literature at which potential injury to the oropharynx of a patient is limited. Thus, at any one hospital facility, the applied pressure difference at a central vacuum line inlet 52 is constant for purposes of maximizing suction efficiency from a central vacuum line inlet 52.

Next, the length of the suction tube 54 must be capable of reaching from the wall inlet 52 to the patient P, limited therefore to no less than 4 feet in length, and has traditionally been found to provide acceptable range at 8 feet in length. Although clearly the length of tubing can be shortened to increase rate of flow, standard practice and experience in hospital settings dictate that 8 feet is a necessary length of tubing associated with emergency facility settings and equipment available for evacuation of vomitus.

The viscosity coefficient for vomitus is also effectively a constant and, for experimentation purposes, has been simulated by vegetable soup. The vomitus must travel from the mouth of the patient P over the length of the tubing 54 plus the length of the suction tip 56 (employed to safely suction the oropharynx of the patient) to a suction canister 58. Although the suction tip adds to the overall length of the tubing, the instrument 56 is commercially produced standard in length and comparable in length to alternate or substitute suction tips used in the medical profession for similar applications. Traditionally, a Standard tip Yankauer suction tip 56 has been the instrument of choice for evacuation of vomitus, having a tip inside diameter of no more than ¼ inch and a length of approximately 12 inches; as such, standard practice and experience in hospital settings dictate that the additional constant length associated with the suction tip for evacuation of vomitus is necessary for safe and efficient procedure.

A suction canister 58 is necessary to collect evacuated vomitus and secretions and is designed to prevent aspiration of foreign material into the central vacuum line inlet 52. A vacuum inlet tube 60 is connected to a vacuum port 62 of the canister lid 70 to create a negative pressure in the canister 58. A standard commercially produced canister 58 provides a ¼ inch patient tubing port 64 for connection of the patient vacuum tubing 54, and a smaller diameter 3/16 inch patient tubing port 66 (shown capped by a removable cap 72). All caps are removable such that ports may be interchangeably used. Suitable connectors 74 may be used as necessary to provide a sealed, continuous path to the suction canister 58. A one inch inside diameter pour spout 68 (shown capped) is provided for removal of the evacuated materials from the canister 58.

Therefore, given the above limiting factors, the radius of the tubing is effectively the only variable by which the rate of flow can be increased to increase suction efficiency in a hospital setting providing a central vacuum line and standard suction equipment.

Figure 1:
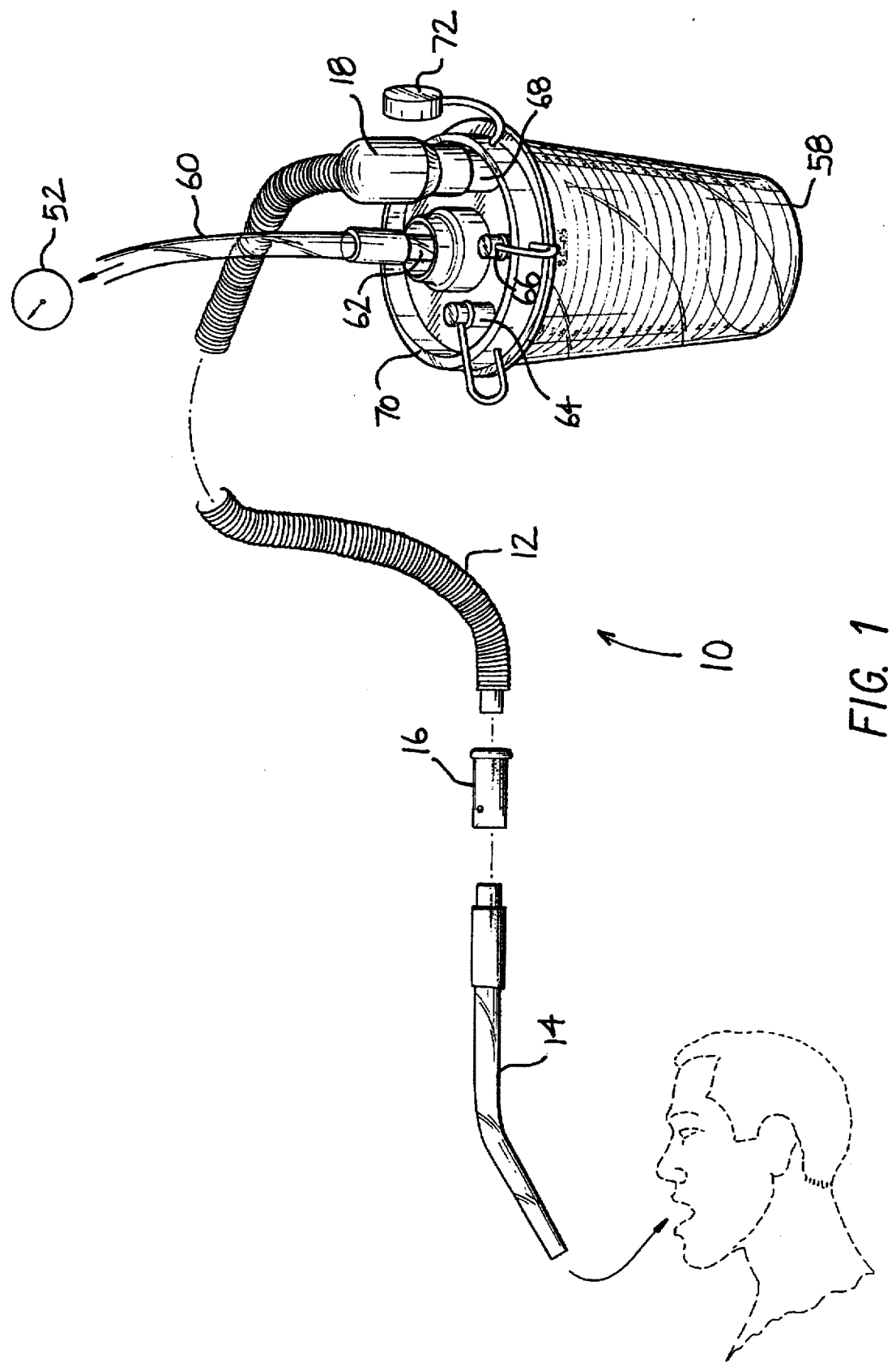
FIG. 1 is an environmental, perspective, exploded view of the oropharyngeal suction device showing its components and connections.

The present invention 10, as shown in FIG. 1, provides a combination of components, in part using components of the equipment as shown in FIG. 2, which are adapted such that patient vacuum tubing having an inside diameter between ½ inch and 1 inch 12 is used. The inventor has determined in experiments simulating evacuation of vomitus (maintaining the above noted constants, using a ¾ inside diameter patient vacuum tubing 12) that vegetable soup is evacuated at a rate at least 10 times faster than the rate of evacuation using the prior art as described in FIG. 2.

The present invention 10 includes a suction tip of increased inside diameter ranging between ½ inch and 1 inch 14, a patient vacuum tubing of an inside diameter between ½ inch to 1 inch and 4 to 10 feet in length 12. Two connectors are provided, a first adapter 18 for connecting the patient vacuum tubing 12 to the 1 inch inside diameter pour spout 68 of a suction canister 58 and a second adapter 16 for connecting the suction tip 14 and the patient vacuum tubing 12. A central vacuum line inlet 52 is provided to apply negative pressure to the canister 58 by means of the vacuum inlet tube 60 attached to the vacuum inlet port 62 of the canister 58. Each of the patient ports 64,66 are capped to provide an airtight seal to maintain the negative pressure within the canister 58.

The combined features of the invention 10, increasing the internal diameters of the patient vacuum tubing 12 and suction tip 14 over the range of ½ inch to 1 inch and the adaptive use of the pour spout 68 to maximize flow rate, positively effect patient mortality and morbidity. However, it is to be understood that the present invention is not limited to the sole embodiment described above, but encompasses any and all embodiments within the scope of the following claims.

I claim:

1. An oropharyngeal suctioning device for evacuation of fluid foreign material including vomitus and bodily secretions, comprising:

a suction tip for insertion into an oropharyngeal cavity of a patient and evacuation of the fluid foreign material, said suction tip having an inside diameter between ½ inch and 1 inch, said diameter being sufficiently large to permit passage of solid particles normally occurring in secretions such as vomitus and further permitting a rapid evacuation rate of the fluid foreign material at an applied negative pressure of no less than 304 mm Hg;

flexible patient vacuum tubing for carrying the fluid foreign material, said patient vacuum tubing having a correspondingly sized inside diameter between ½ inch and 1 inch and being 4 to 10 feet in length, said length being sufficient to enable said suction tip to be operated in the oropharyngeal cavity and further permitting the rapid evacuation rate of the fluid foreign material;

a first flexible adapter connecting said patient vacuum tubing to said suction tip, said first adapter providing an air-tight seal between said patient vacuum tubing and said suction tip;

a suction canister for collection of the fluid foreign material, said suction canister having at least a patient tubing port having a diameter of approximately 3/16 inch, a spout port of at least ½ inch inside diameter and up to 1 inch inside diameter, a vacuum inlet port for attachment of the interior of said canister to a source of negative pressure;

a second flexible adapter connecting said patient vacuum tubing to said spout port, said second adapter providing an air-tight seal between said patient vacuum tubing and said spout port; and a vacuum line operably attached to said vacuum inlet port, said vacuum line providing a source of negative pressure and further providing no less than 304 mm Hg pressure differential at said vacuum inlet port.

2. The oropharyngeal suctioning device according to claim 1, wherein said vacuum line is a central vacuum line in a medical facility.

* * * * *